United States Patent
Koike et al.

(10) Patent No.: US 10,101,284 B2
(45) Date of Patent: Oct. 16, 2018

(54) 3 DIMENSIONAL X-RAY CT APPARATUS, 3 DIMENSIONAL CT IMAGE RECONSTRUCTION METHOD, AND PROGRAM

(71) Applicant: Rigaku Corporation, Akishima-Shi, Tokyo (JP)

(72) Inventors: Takafumi Koike, Tokyo (JP); Yukihiro Hara, Hino (JP)

(73) Assignee: RIGAKU CORPORATION, Tokyo (JP)

( * ) Notice: Subject to any disclaimer, the term of this patent is extended or adjusted under 35 U.S.C. 154(b) by 660 days.

(21) Appl. No.: 13/845,850

(22) Filed: Mar. 18, 2013

(65) Prior Publication Data

US 2013/0279646 A1 Oct. 24, 2013

(30) Foreign Application Priority Data

Apr. 23, 2012 (JP) ................................ 2012-097612

(51) Int. Cl.
*G01N 23/04* (2018.01)
*A61B 6/03* (2006.01)
(Continued)

(52) U.S. Cl.
CPC ........... *G01N 23/046* (2013.01); *A61B 6/032* (2013.01); *A61B 6/508* (2013.01); *A61B 6/504* (2013.01);
(Continued)

(58) Field of Classification Search
CPC ............ G01N 23/046; G01N 2223/419; A61B 6/032; A61B 6/504; A61B 6/508; A61B 6/5229; A61B 6/54
See application file for complete search history.

(56) References Cited

U.S. PATENT DOCUMENTS 5,396,418 A * 3/1995 Heuscher ........................ 378/15
5,513,237 A 4/1996 Nobuta et al.
(Continued)

FOREIGN PATENT DOCUMENTS

DE 102004004603 A1 8/2005
DE 102005018066 A1 10/2006
(Continued)

OTHER PUBLICATIONS

L.A. Feldkamp et al., "Practical cone-beam algorithm", Journal of Optical Society of America A., vol. 1, No. 6, Jun. 1984; 8 pages.

*Primary Examiner* — Glen Kao
(74) *Attorney, Agent, or Firm* — Cantor Colburn LLP

(57) ABSTRACT

Provided are a three-dimensional X-ray CT apparatus, a three-dimensional CT image reconstruction method, and a program, which are capable of reducing an operating time. A three-dimensional X-ray CT apparatus includes: a CT imaging portion for continuously and relatively rotating a measurement system with respect to a subject to perform a CT imaging measurement for taking data on a plurality of transmission images for reconstructing a three-dimensional CT image of the subject; and an image reconstruction portion for reconstructing the three-dimensional CT image based on the data on the plurality of transmission images taken by the CT imaging portion and displaying the three-dimensional CT image. During a period in which the CT imaging measurement is being performed, the image reconstruction portion reconstructs the three-dimensional CT image based on already-taken data on transmission images and displays the three-dimensional CT image before the CT imaging measurement is completed.

11 Claims, 4 Drawing Sheets

(51) Int. Cl.
*G01N 23/046* (2018.01)
*A61B 6/00* (2006.01)

(52) U.S. Cl.
CPC ............... *A61B 6/5229* (2013.01); *A61B 6/54* (2013.01); *G01N 2223/419* (2013.01); *G01N 2223/612* (2013.01)

(56) References Cited

U.S. PATENT DOCUMENTS

| | | | | |
|---|---|---|---|---|
| 5,546,439 | A * | 8/1996 | Hsieh | 378/15 |
| 5,598,453 | A * | 1/1997 | Baba et al. | 378/15 |
| 6,396,898 | B1 * | 5/2002 | Saito | G01N 23/046 378/19 |
| 6,400,789 | B1 * | 6/2002 | Dafni | A61B 6/032 378/15 |
| 2004/0156469 | A1 * | 8/2004 | Nishide | G06T 11/006 378/19 |
| 2005/0203373 | A1 | 9/2005 | Boese | |
| 2005/0249327 | A1 | 11/2005 | Wink et al. | |
| 2006/0036150 | A1 * | 2/2006 | Lutz et al. | 600/407 |
| 2006/0247518 | A1 | 11/2006 | Boing | |
| 2007/0016108 | A1 | 1/2007 | Camus | |
| 2007/0098135 | A1 | 5/2007 | Kunze | |
| 2014/0254748 | A1 * | 9/2014 | Funk | 378/19 |
| 2015/0305696 | A1 * | 10/2015 | Yamakawa | A61B 6/14 378/19 |

FOREIGN PATENT DOCUMENTS

| | | | |
|---|---|---|---|
| DE | 102005032974 A1 | 1/2007 | |
| JP | H07194592 A | 8/1995 | |
| JP | H08117220 A | 5/1996 | |
| JP | 2001330568 A | 11/2001 | |
| JP | 2005528157 A | 9/2005 | |
| JP | 2007117740 A | 5/2007 | |
| JP | 2008228828 A | 10/2008 | |
| JP | WO 2012008492 A1 * | 1/2012 | A61B 6/14 |

* cited by examiner

3 DIMENSIONAL X-RAY CT APPARATUS, 3 DIMENSIONAL CT IMAGE RECONSTRUCTION METHOD, AND PROGRAM

CROSS-REFERENCE TO RELATED APPLICATION

The present application claims priority under 35 U.S.C. § 119 to Japanese application 2012-097612, filed on Apr. 23, 2012, the entire content of which is incorporated herein by reference.

BACKGROUND OF THE INVENTION

1. Field of the Invention

The present invention relates to a three-dimensional X-ray CT apparatus, a three-dimensional CT image reconstruction method, and a program, and more specifically, to an apparatus capable of displaying a three-dimensional CT image a plurality of times based on data on a plurality of transmission images taken in succession.

2. Description of the Related Art

There have conventionally been known X-ray computer tomography (hereinafter referred to as CT) apparatus, which are capable of non-destructive internal measurement and are used not only to a living organism such as a human body and a laboratory animal but also to examination of an internal structure of a product in general, which is a non-living material. Of the X-ray CT apparatus, compared to a two-dimensional X-ray CT apparatus of a step-scan type, helical-scan type, or the like, a three-dimensional X-ray CT apparatus may acquire a three-dimensional image of a subject. The three-dimensional X-ray CT apparatus, which uses an X ray in a shape of a cone beam, irradiates the subject with the X ray, which forms the cone beam, from an X-ray source and detects the X ray that has transmitted through the subject with a two-dimensional detector. The X-ray source and the two-dimensional detector are rotated with respect to the subject to take a plurality of transmission images. Note that, there is also a case where the X-ray source and the two-dimensional detector are fixed and the subject is rotated. A computer included in the three-dimensional X-ray CT apparatus reconstructs a three-dimensional CT image (volume) based on data on the plurality of taken transmission images to display the three-dimensional CT image. A method for the reconstruction of the three-dimensional CT image is disclosed in, for example, JP 2007-117740 A1.

SUMMARY OF THE INVENTION

A three-dimensional CT image of a three-dimensional X-ray CT apparatus may provide more information to a user than a two-dimensional CT image. On the other hand, there is a problem in that the three-dimensional CT image takes time for image reconstruction processing. Therefore, conventionally in the three-dimensional X-ray CT apparatus, after data on a plurality of transmission images is taken while rotating an X-ray source and a two-dimensional detector with respect to a subject, a computer performs processing of reconstructing the three-dimensional CT image based on the data on the plurality of taken transmission images, and then the three-dimensional CT image is displayed. A CT imaging measurement for taking the data on the plurality of transmission images for reconstructing the three-dimensional CT image is hereinafter referred as one measurement.

In the conventional three-dimensional X-ray CT apparatus, one measurement is performed by placing the subject in a measuring field, and after the measurement is finished, the computer reconstructs the three-dimensional CT image based on a result of the measurement to display the three-dimensional CT image. Therefore, it is not until after the display is performed that the user obtains the three-dimensional CT image of the subject, and information on the CT image of the subject cannot be obtained during the measurement. The user cannot judge during the measurement whether a measurement situation satisfies desired conditions, such as whether the subject is placed correctly in the measuring field.

Therefore, the user first performs a measurement for preview (preliminary measurement) for judging the measurement situation. After the measurement for preview is finished, the image reconstruction processing is performed for display so that the user obtains a three-dimensional CT image for preview of the subject. The user judges whether the measurement situation satisfies the desired conditions based on the obtained three-dimensional CT image. When judging that the measurement situation satisfies the desired conditions, the user starts a main measurement for obtaining the three-dimensional CT image of desired image quality. In the conventional three-dimensional X-ray CT apparatus, the measurement for preview is performed and then the computer performs the image reconstruction processing, with the result that in a period in which the user watches the display for making the judgment, the main measurement cannot be started. Therefore, an operating time from the start of the measurement until the three-dimensional CT image of the desired image quality is displayed is increased. The increased operating time may lead to a reduction in image quality of the three-dimensional CT image, such as a change in state of the subject.

The present invention has been made in view of the above-mentioned problems, and therefore has an object to provide a three-dimensional X-ray CT apparatus, a three-dimensional CT image reconstruction method, and a program, which are capable of reducing an operating time.

(1) In order to solve the above-mentioned problems, according to the present invention, there is provided a three-dimensional X-ray CT apparatus, including: a CT imaging portion for continuously rotating relative angular positions of a subject and a measurement system to perform a CT imaging measurement for taking data on a plurality of transmission images for reconstructing a three-dimensional CT image of the subject; and an image reconstruction portion for reconstructing the three-dimensional CT image based on the data on the plurality of transmission images taken by the CT imaging portion, and displaying the three-dimensional CT image. During a period in which the CT imaging measurement is being performed, the image reconstruction portion reconstructs the three-dimensional CT image based on the already-taken data on the transmission images and displays the three-dimensional CT image before the CT imaging measurement is completed.

(2) In the three-dimensional X-ray CT apparatus as described in the above-mentioned item (1), the CT imaging measurement may include taking data on a plurality of transmission images for a primary measurement, and taking data on a plurality of transmission images for a secondary measurement, which is measured in succession to the primary measurement, and the image reconstruction portion may be configured to: reconstruct an initial three-dimensional CT image based on the data on the plurality of transmission images for the primary measurement, and display the initial three-dimensional CT image after the secondary measurement is started; and reconstruct a last three-dimensional CT image based on the data on the plurality of transmission images for the secondary measurement, and display the last three-dimensional CT image.

(3) In the three-dimensional X-ray CT apparatus as described in the above-mentioned item (2), the image reconstruction portion may reconstruct the last three-dimensional CT image based further on the data on the plurality of transmission images for the primary measurement.

(4) In the three-dimensional X-ray CT apparatus as described in the above-mentioned item (2) or (3), the primary measurement may be a measurement for preview for judging a measurement situation, the secondary measurement may be a main measurement for obtaining the three-dimensional CT image of desired image quality, and a rotation speed of a gantry in the primary measurement may be higher than a rotation speed of the gantry in the secondary measurement.

(5) In the three-dimensional X-ray CT apparatus as described in the above-mentioned item (2) or (3), the primary measurement and the secondary measurement may constitute a main measurement for obtaining the three-dimensional CT image of desired image quality, and a rotation speed of a gantry in the primary measurement may be equal to a rotation speed of the gantry in the secondary measurement.

(6) In the three-dimensional X-ray CT apparatus as described in any one of the above-mentioned items (2) to (5), the primary measurement may be taking the data on the plurality of transmission images necessary for the image reconstruction portion to perform 180° image reconstruction.

(7) In the three-dimensional X-ray CT apparatus as described in the above-mentioned item (4), in the secondary measurement, the gantry may have a rotation range of 360° multiplied by a natural number.

(8) In the three-dimensional X-ray CT apparatus as described in the above-mentioned item (5), when the primary measurement and the secondary measurement are combined, the gantry may have a rotation range of 360° multiplied by a natural number.

(9) In the three-dimensional X-ray CT apparatus as described in any one of the above-mentioned items (2) to (8), the secondary measurement may include a plurality of submeasurements, and the image reconstruction portion may reconstruct an intermediate three-dimensional CT image based on data on a plurality of transmission images for an initial submeasurement of the plurality of submeasurements, and display the intermediate three-dimensional CT image after a submeasurement next to the initial submeasurement is started.

(10) In the three-dimensional X-ray CT apparatus as described in the above-mentioned item (9), the image reconstruction portion may reconstruct the intermediate three-dimensional CT image based further on the data on the plurality of transmission images for the primary measurement.

(11) In the three-dimensional X-ray CT apparatus as described in the above-mentioned item (2), the image reconstruction portion may include: an input image data generating section for generating data on a plurality of input images based on the data on the plurality of transmission images taken by the CT imaging portion; and a reconstruction processing section for subjecting the data on the plurality of input images to reconstruction processing to generate the three-dimensional CT image, in parallel to the primary measurement, the input image data generating section may generate the data on the plurality of input images by using at least a part of the data on the plurality of transmission images for the primary measurement, and the reconstruction processing section may subject the data on the plurality of input images to the reconstruction processing to generate the initial three-dimensional CT image, and in parallel to the secondary measurement, the input image data generating section may generate the data on the plurality of input images by using at least a part of the data on the plurality of transmission images for the secondary measurement, and the reconstruction processing section may subject the data on the plurality of input images to the reconstruction processing to generate the last three-dimensional CT image.

(12) In the three-dimensional X-ray CT apparatus as described in the above-mentioned item (11), when the part of the data on the plurality of transmission images for the secondary measurement includes data on a plurality of transmission images from the same angular position of a gantry, the input image data generating section may weight the data on the plurality of transmission images in accordance with a rotation speed of the gantry and combine the weighted data on the plurality of transmission images to generate data on an input image at the angular position.

(13) In the three-dimensional X-ray CT apparatus as described in the above-mentioned item (3), the image reconstruction portion may include: an input image data generating section for generating data on a plurality of input images based on the data on the plurality of transmission images taken by the CT imaging portion; and a reconstruction processing section for subjecting the data on the plurality of input images to reconstruction processing to generate the three-dimensional CT image, in parallel to the primary measurement, the input image data generating section may generate the data on the plurality of input images by using at least a part of the data on the plurality of transmission images for the primary measurement, and the reconstruction processing section may subject the data on the plurality of input images to the reconstruction processing to generate the initial three-dimensional CT image, and in parallel to the secondary measurement, the input image data generating section may generate the data on the plurality of input images by using at least a part of the data on the plurality of transmission images for the primary measurement and at least a part of the data on the plurality of transmission images for the secondary measurement, and the reconstruction processing section may subject the data on the plurality of input images to the reconstruction processing to generate the last three-dimensional CT image.

(14) In the three-dimensional X-ray CT apparatus as described in the above-mentioned item (13), when the part of the data on the plurality of transmission images for the primary measurement and the part of the data on the transmission images for the secondary measurement include data on a plurality of transmission images from the same angular position of a gantry, the input image data generating section may weight the data on the plurality of transmission images in accordance with a rotation speed of the gantry and combine the weighted data on the plurality of transmission images to generate data on an input image at the angular position.

(15) According to the present invention, there may be provided a three-dimensional X-ray CT image reconstruction method for continuously rotating relative angular positions of a subject and a measurement system to perform a CT imaging measurement for taking data on a plurality of transmission images for reconstructing a three-dimensional CT image of the subject, and reconstructing the three-dimensional CT image based on the taken data on the plurality of transmission images and displaying the three-dimensional CT image, the CT imaging measurement including taking data on a plurality of transmission images for a primary measurement, and taking data on a plurality of transmission images for a secondary measurement, which is measured in succession to the primary measurement, the three-dimensional X-ray CT image reconstruction method including: a primary measurement and reconstruction step of reconstructing an initial three-dimensional CT image based on the data on the plurality of transmission images for the primary measurement, and displaying the initial three-dimensional CT image after the secondary measurement is started; and a secondary measurement and reconstruction step of reconstructing a last three-dimensional CT image based on the data on the plurality of transmission images for the secondary measurement, and displaying the last three-dimensional CT image.

(16) According to the present invention, there may be provided a program for causing a computer to function as, the computer being included in a three-dimensional X-ray CT apparatus for continuously rotating relative angular positions of a subject and a measurement system to perform a CT imaging measurement for taking data on a plurality of transmission images for reconstructing a three-dimensional CT image of the subject, and reconstructing the three-dimensional CT image based on the taken data on the plurality of transmission images and displaying the three-dimensional CT image, the CT imaging measurement including taking data on a plurality of transmission images for a primary measurement, and taking data on a plurality of transmission images for a secondary measurement, which is measured in succession to the primary measurement: primary measurement and reconstruction means for reconstructing an initial three-dimensional CT image based on the data on the plurality of transmission images for the primary measurement, and displaying the initial three-dimensional CT image after the secondary measurement is started; and secondary measurement and reconstruction means for reconstructing a last three-dimensional CT image based on the data on the plurality of transmission images for the secondary measurement, and displaying the last three-dimensional CT image.

According to the present invention, it is possible to provide a three-dimensional X-ray CT apparatus, a three-dimensional CT image reconstruction method, and a program, which are capable of reducing an operating time.

DETAILED DESCRIPTION OF THE INVENTION

Now, embodiments of the present invention are specifically described in detail with reference to the drawings. It should be noted, however, that the figures described below are merely used for exemplifying the embodiments and are not necessarily drawn to the scale described in the embodiments. Note that, in the figures described below, the members having the same function are denoted by the same reference symbol, and repetitive description thereof is omitted except where necessary.

First Embodiment

A three-dimensional X-ray CT apparatus according to a first embodiment of the present invention is a three-dimensional X-ray micro-CT apparatus for taking a CT image of a small animal such as a laboratory mouse. In the three-dimensional X-ray CT apparatus, a gantry including an X-ray source for irradiating a subject with an X ray, which forms a cone beam, and a two-dimensional detector placed opposite to the X-ray source with respect to the subject, rotates. Then, a three-dimensional CT image is reconstructed by cone-beam reconstruction using the Feldkamp method. Note that, the image reconstruction technology relating to the Feldkamp method is disclosed in Journal of Optical Society of America A., Vol. 1, No. 6, page 612, 1984. Description is given herein of a three-dimensional X-ray micro-CT apparatus for a small animal. However, it should be understood that the present invention is not limited thereto, and another three-dimensional X-ray CT apparatus may be employed.

(Configuration of Three-Dimensional X-Ray CT Apparatus)

Figure 1:
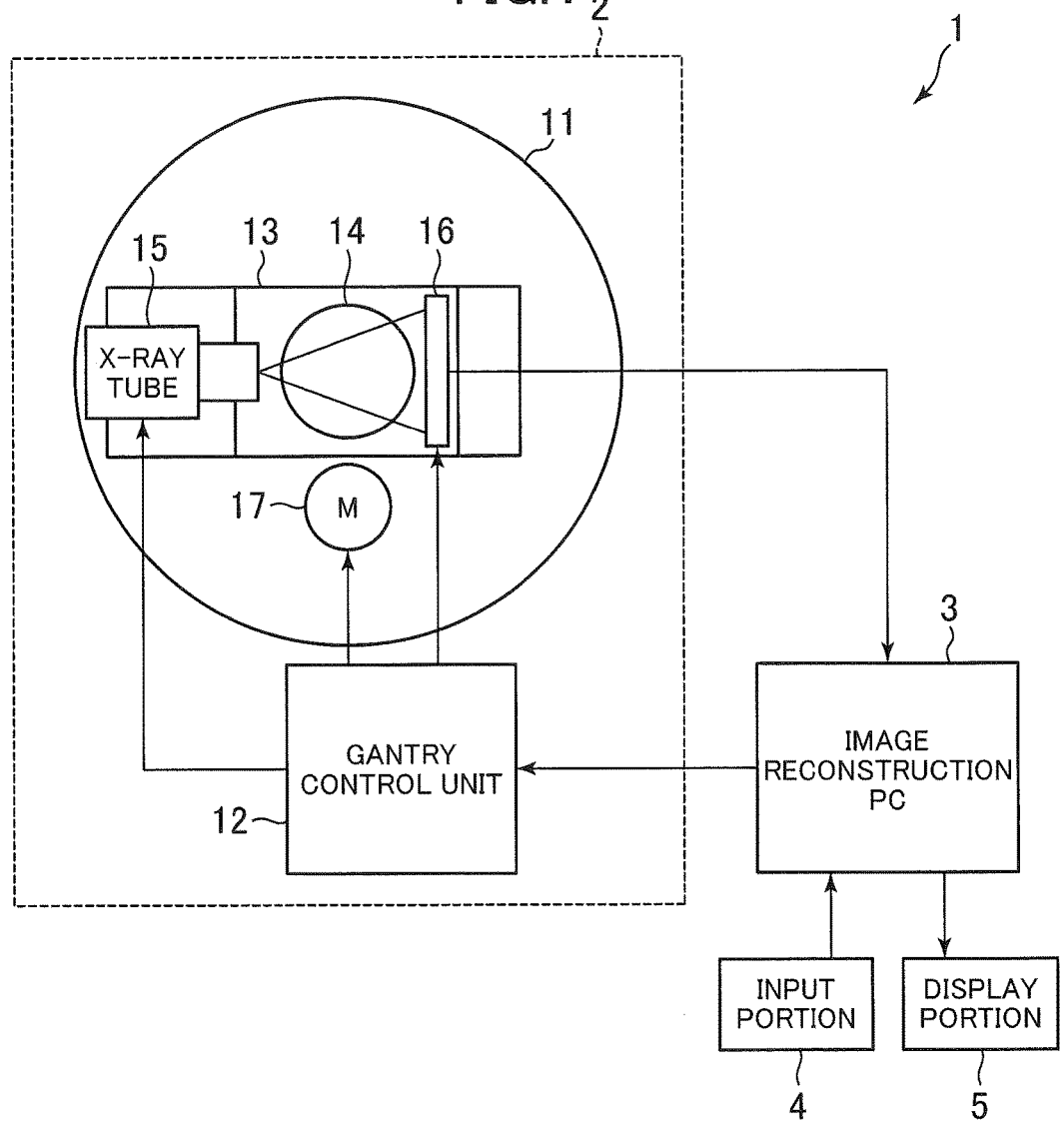
FIG. 1 is a schematic diagram illustrating structure of a three-dimensional X-ray CT apparatus according to embodiments of the present invention.

FIG. 1 is a schematic diagram illustrating structure of a three-dimensional X-ray CT apparatus 1 according to the first embodiment of the present invention. As illustrated in FIG. 1, the three-dimensional X-ray CT apparatus 1 according to this embodiment includes a CT imaging portion 2, an image reconstruction PC 3, an input portion 4, and a display portion 5. The CT imaging portion 2 includes a gantry 11 and a gantry control unit 12, and the gantry 11 includes a rotating arm 13, a holding stage 14, an X-ray tube 15, a two-dimensional detector 16, and an arm rotation motor 17. Note that, with the subject held on the holding stage 14 as the center, the X-ray tube 15 and the two-dimensional detector 16 are fixed to the rotating arm 13 so as to be opposed to each other. The rotating arm 13 is placed in the gantry 11 so as to be rotatable with respect to the subject. The X-ray tube 15 serving as the X-ray source emits the X ray, which forms the cone beam. The X ray irradiates the subject, and the X ray that has been transmitted through the subject is received by the two-dimensional detector 16. The two-dimensional detector 16 includes a receiving surface for receiving the X ray, in which U×V pixels are arranged so as to form a panel. The two-dimensional detector 16 detects the X ray that has been transmitted through the subject as a projection image of U×V pixels. In this case, the projection image serves as data on a transmission image. The arm rotation motor 17 rotates the rotating arm 13, to thereby rotate the entire gantry 11 continuously. By the continuous rotation of the gantry 11, CT imaging measurements for taking data on a plurality of transmission images in succession may be performed continuously. Note that, the arm rotation motor 17 is capable of such setting as to obtain a desired rotation speed in taking the data on each transmission image. Further, after taking the data is finished, the gantry 11 may be returned to an original position.

Note that, in this case, a measurement system including the X-ray source and the two-dimensional detector is rotated by a rotation driving system (rotating arm) with respect to the subject held on the holding stage. The present invention is not limited to this case, but may also be applied to a case where the holding stage for holding the subject includes a rotation driving system, which rotates the subject with respect to a fixed measurement system. The two-dimensional detector is placed opposite to the X-ray source with respect to the subject. Relative angular positions of the subject and the measurement system are rotated continuously so that the two-dimensional detector may detect data on the transmission images from the X-ray source, which is placed at a different angle with respect to the subject.

(Configuration of Image Reconstruction PC)

Figure 2:
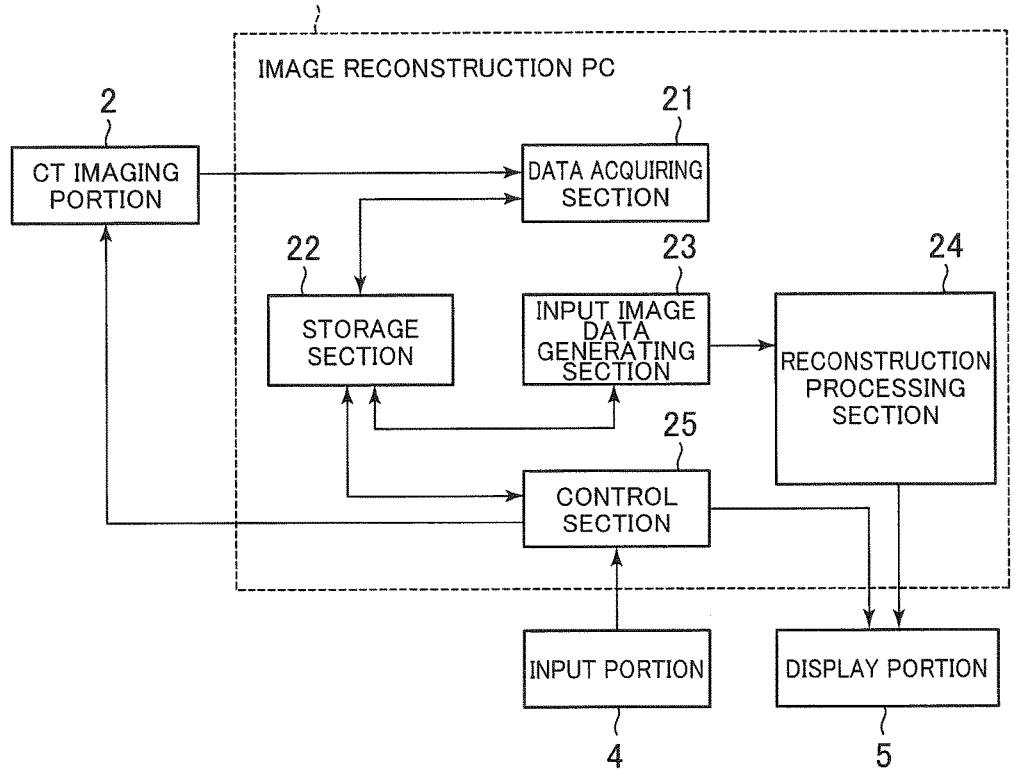
FIG. 2 is a block diagram of the three-dimensional X-ray CT apparatus according to the embodiments of the present invention.

FIG. 2 is a block diagram of the three-dimensional X-ray CT apparatus 1 according to this embodiment. The image reconstruction PC 3 is a computer for reconstructing the three-dimensional CT image based on the data on the plurality of transmission images taken by the CT imaging portion 2, and serves as an image reconstruction portion. The image reconstruction PC 3 includes a data acquiring section 21, a storage section 22, an input image data generating section 23, a reconstruction processing section 24, and a control section 25.

The data acquiring section 21 acquires the data on the transmission images of the subject from the CT imaging portion 2. The storage section 22 stores the acquired data on the transmission images of the subject, stores input image data, which is to be described below, and further stores data on the three-dimensional CT image, which is to be described below. The input image data generating section 23 uses the acquired data on the transmission images to generate the input image data for input to the reconstruction processing section 24, and outputs the generated input image data to the storage section 22 and the reconstruction processing section 24. The storage section 22 stores the input image data. The reconstruction processing section 24 is a graphics processing unit (GPU), which is a processor for increasing the speed of graphics processing. The GPU is used as the reconstruction processing section 24 to enable parallel processing, which is to be described below. The reconstruction processing section 24 performs the reconstruction processing on the input image data by the Feldkamp method to generate the three-dimensional CT image, and outputs the generated three-dimensional CT image to the storage section 22 and the display portion 5. The storage section 22 stores the three-dimensional CT image, and the display portion 5 displays the three-dimensional CT image.

The input portion 4 includes a keyboard and a mouse to enable a user to input measurement settings and the like to the input portion 4, which outputs the input information to the control section 25. The control section 25 outputs the input information to the gantry control unit 12, which controls a rotation speed ω and the like of the gantry 11 to perform the CT imaging measurements for taking the data on the transmission images.

The display portion 5 includes a display to display the settings of the CT imaging measurements as well as the three-dimensional CT image, which is input from the reconstruction processing section 24 or the storage section 22 of the image reconstruction PC 3. At this time, the user inputs display conditions and the like to the input portion 4, which outputs the input information to the control section 25. The control section 25 displays the three-dimensional CT image based on the input information. In this case, the display conditions include, for example, a direction in which the three-dimensional CT image is viewed, a cross-section in a case where a two-dimensional cross-section is to be displayed, and a display part in a case where a particular part (for example, blood vessel) of the three-dimensional CT image is to be displayed.

(Feldkamp Method)

Next, description is given of reconstruction methods for the three-dimensional CT image. In this embodiment, the Feldkamp method is used for the reconstruction of the three-dimensional CT image. The input image data generating section 23 generates the input image data constituted of a plurality of projection images (data on the transmission images) and outputs the generated input image data to the reconstruction processing section 24. In this case, one projection image is X-ray intensity information of U×V pixels. The reconstruction processing section 24 includes a plurality of memories, and the input image data generating section 23 transfers one of M projection images to a memory. The one projection image stored in the memory is subjected to filtering processing and reverse projection processing, and an obtained result is added to a volume stored in another memory. This series of processing is repeated for all the M projection images, to thereby obtain the added volume, which forms the reconstructed three-dimensional CT image. The reconstruction processing section 24 outputs the three-dimensional CT image to the storage section 22, which stores the three-dimensional CT image.

The reconstruction methods for the three-dimensional CT image include a 180° image reconstruction method and a 360° image reconstruction method. In the 360° image reconstruction method, the data on the plurality of transmission images taken in a 360° measuring range (full scan) is used, and the input image data generating section 23 generates the input image data to be input to the reconstruction processing section 24, which performs the reconstruction processing on the input image data to generate the three-dimensional CT image. For example, when angular positions θ are set from 0° at intervals of 3°, the CT imaging portion 2 takes the data on (a total of 120) transmission images at the angular positions where θ=3(m−1) (m=1, 2, . . . 120). The input image data generating section 23 of the image reconstruction PC 3 generates the input image data by setting the data on the 120 transmission images, which are taken by the CT imaging portion 2, as the data on the same number of input images. Then, the reconstruction processing section 24 of the image reconstruction PC 3 reconstructs the three-dimensional CT image based on the input image data. A case where the measuring range exceeds 360° is described later.

On the other hand, in the 180° image reconstruction method, based on the data on the plurality of transmission images taken in the measuring range of about 180° (half scan), the input image data generating section 23 generates the input image data to be input to the reconstruction processing section 24, which reconstructs the three-dimensional CT image. For example, when the angular positions θ are set from 0° at intervals of 3°, the CT imaging portion 2 takes the data on (a total of 60) transmission images at the angular positions where θ=3(m−1) (m=1, 2, . . . 60). The X-ray tube 15 of the three-dimensional X-ray CT apparatus 1 according to this embodiment irradiates the subject with the X ray, which forms the cone beam. Therefore, when the three-dimensional CT image is reconstructed based on the data on the plurality of transmission images taken in the measuring range of just 180°, the input image data is insufficient in terms of symmetry, and hence an artifact occurs in the reconstructed three-dimensional CT image. The CT imaging portion 2 further takes the data on 6(≈20/3) transmission images, which are taken in the measuring range of a fan angle α (about 20°) of the cone beam. The input image data generating section 23 of the image reconstruction PC 3 generates the input image data by setting the data on the total of 66 transmission images as the data on the same number of input images. Then, the reconstruction processing section 24 of the image reconstruction PC 3 reconstructs the three-dimensional CT image based on the input image data (180° image reconstruction method).

The structure of the three-dimensional X-ray CT apparatus 1 according to this embodiment has been described above. The three-dimensional X-ray CT apparatus 1 according to this embodiment has a feature in the reconstruction processing section 24 of the image reconstruction PC 3, and in that in parallel to the processing in which the gantry control unit 12 rotates the gantry 11 to perform the CT imaging measurements, the reconstruction processing section 24 performs the reconstruction processing of the three-dimensional CT image. The three-dimensional CT image is reconstructed during the CT imaging measurements based on the data on the transmission images, which have already been taken, and the reconstructed three-dimensional CT image may be displayed before the CT imaging measurements are completed. When the CT imaging measurements include taking the data on M (where M is an integer of 2 or more) transmission images for a primary measurement and taking the data on N (where N is an integer of 2 or more) transmission images for a secondary measurement, which is performed in succession to the primary measurement, the data on the M transmission images for the primary measurement and the data on the N transmission images for the secondary measurement are taken in succession. At the same time, the initial three-dimensional CT image is reconstructed based on the data on the M transmission images for the primary measurement, and after the secondary measurement is started, the initial three-dimensional CT image may be displayed. Further, the last three-dimensional CT image is reconstructed based on the data on the transmission images for the secondary measurement, and the last three-dimensional CT image is displayed.

(Three-Dimensional CT Image Reconstruction Methods)

Figure 3:
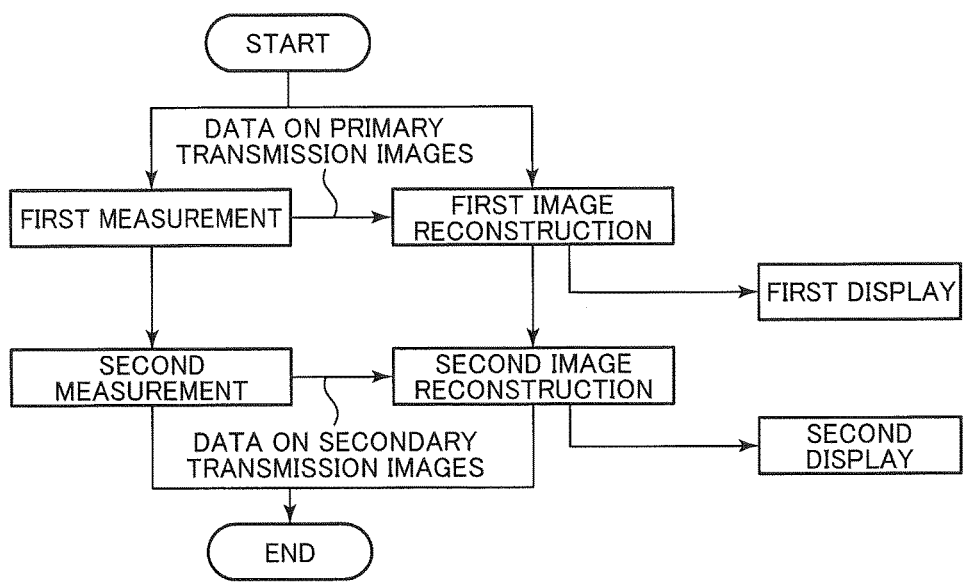
FIG. 3 is a flow chart of processing of the three-dimensional X-ray CT apparatus according to first to fifth embodiments of the present invention.

Next, description is given of operation of the three-dimensional X-ray CT apparatus 1 configured as described above. FIG. 3 is a flow chart of processing of the three-dimensional X-ray CT apparatus 1 according to this embodiment. As illustrated in FIG. 3, in the flow chart of the processing according to this embodiment, the CT imaging measurements performed by the CT imaging portion 2, which are illustrated on the left, and three-dimensional CT image reconstruction performed by the image reconstruction PC 3, which is illustrated on the right, are performed in parallel. For example, the first measurement and the first image reconstruction are performed in parallel by the CT imaging portion 2 and the image reconstruction PC 3, respectively. Note that, as described above, the CT imaging measurement for taking the data on the plurality of transmission images for reconstructing the three-dimensional CT image is referred to as "one measurement".

Of the CT imaging measurements performed by the CT imaging portion 2, the taking of the data on the M transmission images for the primary measurement and the taking of the data on the N transmission images for the secondary measurement are hereinafter referred to as the first measurement and the second measurement, respectively. In the CT imaging measurements performed by the CT imaging portion 2, the first measurement and the second measurement are performed in succession. The phrase "the first measurement and the second measurement are performed in succession" as used herein means that after the first measurement is finished, the second measurement is started without a time interval for the input operation by the user or the like. The image reconstruction PC 3 reconstructs the first three-dimensional CT image (initial three-dimensional CT image) from the first measurement, and then displays the first three-dimensional CT image (first display), which is the initial display. The first measurement and the second measurement are performed in succession, and hence the second measurement is started before the first display is performed.

In this embodiment, the first measurement is a measurement for preview (preliminary measurement) for judging a measurement situation, and the second measurement is a main measurement for obtaining the three-dimensional CT image of desired image quality. The first measurement as the measurement for preview is desirably high in rotation speed $\omega_1$ of the gantry 11 so that a three-dimensional CT image for preview may be displayed earlier. The second measurement as the main measurement is desirably low in rotation speed $\omega_2$ of the gantry 11 so that the three-dimensional CT image of higher image quality may be displayed. In other words, it is desired that $\omega_1$ be higher than $\omega_2$ to satisfy the following relationship: $\omega_1 > \omega_2$. Further, the first measurement has the measuring range set to the half scan (180°+α) so that the three-dimensional CT image for preview may be displayed earlier, and the second measurement, which is performed as the main measurement, has the measuring range set to the full scan (360°). Due to the differences in rotation speed of the gantry 11 and in measuring range, measuring time of the first measurement is about 10 [sec], and measuring time of the second measurement is 8 [min] (=480 [sec]). In this case, the measuring time of the first measurement is about 10 [sec] because the measuring range is 180°+α, and when the measurement is performed for the measuring range of just 180° at the rotation speed $\omega_1$ of the gantry 11, the measuring time becomes just 10 [sec].

When the CT imaging portion 2 starts the first measurement, the image reconstruction PC 3 performs the first image reconstruction in parallel with the measurement. In the first measurement, the CT imaging portion 2 takes the data on the M (in this case, 66) transmission images sequentially while rotating the gantry 11 at the rotation speed $\omega_1$. When the data on the transmission images has been taken, the CT imaging portion 2 transfers the data on the transmission images sequentially to the image reconstruction PC 3, and the data acquiring section 21 of the image reconstruction PC 3 acquires the data on the transmission images. Now, the data on the k-th (where k is any integer of 1 or more and M or less) transmission image of the data on the M transmission images is described. The data on the k-th transmission image is the X-ray intensity information (projection image) of U×V pixels and is represented by I(u, v, k). Note that, u and v represent coordinates of U×V pixels, and are any integers that satisfy the following relationships: $1 \leq u \leq U$; and $1 \leq v \leq V$. The data on the transmission images acquired by the data acquiring section 21 is input to and stored in the storage section 22 and is input to the input image data generating section 23. The input image data generating section 23 stores the data on the k-th transmission image I(u, v, k) as the data on the k-th input image J(u, v, k). When the data on the transmission image taken in the first measurement and the input image data generated by the input image data generating section 23 in the first image reconstruction are defined here as data on a primary transmission image $I_1(u, v, k)$ and data on a primary input image $J_1(u, v, k)$, respectively, the following relationship is satisfied: $J_1(u, v, k) = I_1(u, v, k)$.

As described above, after generating the data on the k-th primary input image (projection image) $J_1(u, v, k)$, the input image data generating section 23 transfers the generated data on the k-th primary input image sequentially to the reconstruction processing section 24. The reconstruction processing section 24 subjects the data on the k-th primary input image $J_1(u, v, k)$ to the filtering processing and the reverse projection processing by the 180° image reconstruction method, and adds the result to the volume. The volume obtained by repeating the processing sequentially is the first three-dimensional CT image (initial three-dimensional CT image).

The gantry 11 rotates continuously, and after the first measurement is finished, the CT imaging portion 2 changes the rotation speed of the gantry 11 to the rotation speed $\omega_2$ to start the second measurement without an interval. The image reconstruction PC 3 reconstructs the first three-dimensional CT image (initial three-dimensional CT image) in the first image reconstruction. The first three-dimensional CT image from the reconstruction processing section 24 is input to and stored in the storage section 22, and is input to the display portion 5 so that the first three-dimensional CT image is displayed (first display) on the display of the display portion 5 after about 10 [sec] since the start of the operation, which is the initial three-dimensional CT image display.

When the CT imaging portion 2 starts the second measurement, the image reconstruction PC 3 performs the second image reconstruction in parallel with the measurement. In the second measurement, the CT imaging portion 2 takes the data on the transmission images sequentially while rotating the gantry 11 at the rotation speed $\omega_2$ in the 360° measuring range, and transfers the data on the transmission images sequentially to the image reconstruction PC 3. The measuring range of the second measurement is 360°. Therefore, when expressed from the angular position $\theta=0$ at which the first measurement is started, the measuring range of the second measurement is from $\theta=180°+\alpha$ to $\theta=540°+\alpha$. When the measurement is performed at the same angular interval (3°) as in the first measurement, the data on the N (in this case, 120) transmission images is taken in the second measurement. Now, the data on the k-th (where k is any integer of 1 or more and N or less) transmission image of the data on the N transmission images is described. Further, the data on the transmission image taken in the second measurement and the data on the input image generated by the input image data generating section 23 in the second image reconstruction are defined here as data on secondary transmission image $I_2(u, v, k)$ and data on secondary input image $J_2(u, v, k)$, respectively. The input image data generating section 23 stores the data on the k-th secondary transmission image $I_2(u, v, k)$ as the data on the k-th secondary input image $J_2(u, v, k)$. In other words, the following relationship is satisfied: $J_2(u, v, k)=I_2(u, v, k)$.

As in the first image reconstruction, after generating the data on the k-th secondary input image $J_2(u, v, k)$, the input image data generating section 23 transfers the generated data on the k-th secondary input image sequentially to the reconstruction processing section 24. As opposed to the first image reconstruction, the reconstruction processing section 24 subjects the data on the k-th secondary input image $J_2(u, v, k)$ to the filtering processing and the reverse projection processing by the 360° image reconstruction method, and adds the result to the volume. The volume obtained by repeating the processing sequentially is the second three-dimensional CT image (last three-dimensional CT image). By the reconstruction processing section 24, the second three-dimensional CT image is input to and stored in the storage section 22, and is input to the display portion 5 so that the second three-dimensional CT image is displayed (second display) on the display of the display portion 5 after about 8 [min] since the start of the operation, which is the last three-dimensional CT image. This completes the operation of the three-dimensional X-ray CT apparatus 1.

The first measurement in this embodiment is the measurement for preview for judging whether the measurement situation satisfies desired conditions, such as whether the subject is correctly held on the holding stage and whether the subject is correctly set in a measuring field, and has the rotation speed of the gantry set to be high, with the result that the measuring time is short. On the other hand, when the measurement situation satisfies the desired conditions, the second measurement is the main measurement for obtaining the three-dimensional CT image of high image quality, and has the rotation speed of the gantry set to be low, with the result that the measuring time is long.

As described above, with the conventional three-dimensional X-ray CT apparatus, the computer performs image reconstruction processing after performing the primary measurement, which serves as the measurement for preview, and hence a certain period of time is required to display the three-dimensional CT image based on the measurement result of the measurement for preview after the measurement is finished. Further, the secondary measurement, which serves as the main measurement, is started after the user watches the display to judge whether or not the measurement situation satisfies the desired conditions, and hence a downtime occurs from the end of the primary measurement to the start of the secondary measurement. In contrast, with the three-dimensional X-ray CT apparatus according to this embodiment, the CT imaging portion 2 performs the primary measurement and the secondary measurement in succession so that such downtime does not occur. The image reconstruction PC 3 performs the image reconstruction processing in parallel with the measurements performed by the CT imaging portion 2, and hence after the primary measurement is finished, the time until the initial three-dimensional CT image is displayed is significantly reduced as compared to the conventional three-dimensional X-ray CT apparatus. Then, after the secondary measurement is started, the user makes the judgment based on the display of the initial three-dimensional CT image. When the measurement satisfies desired measurement conditions, the measurement may be continued, and when the measurement does not satisfy desired measurement conditions, the operation may be stopped by manual control. Further, the time after the secondary measurement is finished until the last three-dimensional CT image is displayed is also reduced as compared to the conventional three-dimensional X-ray CT apparatus, and hence an operating time from the start of the measurement until the desired three-dimensional CT image is displayed is reduced.

Second Embodiment

Structure of a three-dimensional X-ray CT apparatus 1 according to a second embodiment of the present invention is the same as the structure of the three-dimensional X-ray CT apparatus 1 according to the first embodiment except that operation is different. The three-dimensional CT apparatus 1 according to this embodiment is different in operation from the three-dimensional X-ray CT apparatus 1 according to the first embodiment in that the last three-dimensional CT image is reconstructed based not only on the data on the transmission images for the secondary measurement but also on the data on the transmission images for the primary measurement. To be specific, the input image data generating section 23 of the image reconstruction PC 3 generates the data on the secondary input images based on the data on the primary transmission images and the data on the secondary transmission images.

The operation of the three-dimensional X-ray CT apparatus 1 according to this embodiment is described. The operation according to this embodiment is represented by the flow chart of the processing illustrated in FIG. 3 as in the first embodiment. The primary measurement (first measurement) and the secondary measurement (second measurement) in this embodiment are the same as those of the first embodiment. Further, the first image reconstruction is also the same as that of the first embodiment. Accordingly, description is given of the generation of the data on the secondary input images in the second image reconstruction, which is different from that of the first embodiment.

In the first image reconstruction, the data on M (in this case, 66) primary input images $J_1(u, v, k)$ (=$I_2(u, v, k)$) is generated. In this case, k is any integer that satisfies the following relationship: $1 \leq k \leq M$. In other words, the data on the (M+1)th and subsequent input images is not generated in the first image reconstruction. Therefore, in the second image reconstruction, of the data on the N transmission images taken in succession in the second measurement, the data on the first (N−M) transmission images is stored as the data on (N−M) input images subsequent to the data on the M input images generated in the first image reconstruction. In other words, in the second measurement, the data on the first (N−M) transmission images corresponds to the range of from $\theta=180°+\alpha$ to $\theta=360°$ when expressed from the angular position $\theta=0$ at which the first measurement is started, and the data on the p-th ($1 \leq p \leq N-M$) transmission image included in the data on the first (N−M) transmission images corresponds to the data on the k-th ($M+1 \leq k \leq N$) input image, where k=p+M. Therefore, the data on the transmission image and the data on the input image are represented by using k, which represents the corresponding angular position. Specifically, such data on the transmission image is stored as the data on the secondary transmission image $I_2(u, v, k)$, which is stored as the data on the secondary input image $J_2(u, v, k)$, and hence the following relationship is satisfied: $J_2(u, v, k) = I_2(u, v, k)$ (provided that $M+1 \leq k \leq N$).

In contrast, in the first image reconstruction, the data on the M primary input images is generated. Therefore, the data on the last M transmission images of the data on the N transmission images taken in succession in the second measurement, and the data on the M primary input images generated in the first image reconstruction are data from the same angular position of the gantry 11. In the second image reconstruction, the pieces of data at the same angular position are weighted in accordance with the rotation speed of the gantry 11 and combined, to thereby obtain the data on the secondary input images. In other words, in the second measurement, the data on the last M transmission images corresponds to the range of from $\theta=0°$ to $\theta=180°+\alpha$ when expressed from the angular position $\theta=0$ at which the first measurement is started, and the data on the p-th (N−M+$1 \leq p \leq N$) transmission image included in the data on the last M transmission images corresponds to the data on the k-th ($1 \leq k \leq M$) input image, where k=p−(N−M). Therefore, such data on the transmission image is represented as the data on the secondary transmission image $I_2(u, v, k)$ by using k, which represents the corresponding angular position. Then, the data on the secondary input image $J_2(u, v, k)$ generated by the input image data generating section 23 may be expressed by (Equation 1) below for k that satisfies $1 \leq k \leq M$.

$$J_2(u, v, k) = \frac{T_1 \cdot J_1(u, v, k) + t_2 \cdot I_2(u, v, k)}{T_1 + t_2} = \frac{t_1 \cdot I_1(u, v, k) + t_2 \cdot I_2(u, v, k)}{t_1 + t_2}$$ [Equation 1]

$T_1$ in (Equation 1) is a weighting factor for the data on the primary input image $J_1(u, v, k)$, and $t_1$ and $t_2$ are weighting factors for the data on the primary transmission image $I_1(u, v, k)$ and the data on the secondary transmission images $I_2(u, v, k)$. Those weighting factors are defined depending on the rotation speed $\omega$ of the gantry 11. The rotation speed $\omega_1$ in the first measurement and the rotation speed $\omega_2$ in the second measurement are expressed with the measuring time and the measuring range as $T_1=t_1 \propto 1/\omega_1$ and $t_2 \propto 1/\omega_2$, and may be expressed in terms of measuring time as $T_1=t_1=10\cdot 2=20$ and $t_2=480$. Note that, as described above, the data on the primary input image $J_1(u, v, k)$ is equivalent to the data on the primary transmission image $I_1(u, v, k)$. Through the multiplication with values as weights obtained by dividing the weighting factors by the factors in the denominator of Equation 1, the data on the secondary transmission image and the data on the primary input image (data on the primary transmission image) are weighted and added (combined) to generate the data on the secondary input image. Such combination improves an S/N ratio of the data.

In summary, the data on the secondary input image $J_2(u, v, k)$ may be expressed by (Equation 1) for k that satisfies $1 \leq k \leq M$ and by $J_2(u, v, k) = I_2(u, v, k)$ for k that satisfies $M+1 \leq k \leq N$.

In this manner, when the 180° image reconstruction method is used to reconstruct the initial three-dimensional CT image, the data on the input images for the 180° image reconstruction method is the data on the input images corresponding to 180°+α (α is the fan angle). When the 360° image reconstruction method is used to reconstruct the three-dimensional CT image, the data on the input images corresponding to 360° is necessary, and based on the data on the transmission images at the angular positions exceeding 180°+α, the data on the input images at the angular positions exceeding 180°+α is generated. Once the data on the input images corresponding to 360° is generated, the data on the transmission images at the angular positions θ exceeding 360° and the data on the input images at the corresponding angular positions (θ−360·n) are weighted and combined to newly obtain the data on the input images. Therefore, the data improved in S/N ratio may be obtained, and the image quality of the reconstructed three-dimensional CT image may be improved.

In the image reconstruction processing according to the first embodiment, only the data on the transmission images for the secondary measurement is used for the reconstruction of the last three-dimensional CT image. In contrast, in the image reconstruction processing according to this embodiment, not only the data on the transmission images for the secondary measurement but also the data on the transmission images for the primary measurement is used for the reconstruction of the last three-dimensional CT image. Therefore, according to the three-dimensional X-ray CT apparatus of this embodiment, in addition to the effect provided by the first embodiment, the image quality of the three-dimensional CT image displayed in displaying the last three-dimensional CT image may be improved further than in the first embodiment.

Third Embodiment

Structure of a three-dimensional X-ray CT apparatus 1 according to a third embodiment of the present invention is the same as the structure of the three-dimensional X-ray CT apparatus 1 according to the first and second embodiments except that operation is different. The three-dimensional CT apparatus 1 according to this embodiment is different in operation from the three-dimensional X-ray CT apparatus 1 according to the first and second embodiments in that the first measurement (primary measurement) and the second measurement (secondary measurement) have the same rotation speed ω of the gantry 11 and the same measuring range of 360°. In this case, the first measurement and the second measurement constitute the main measurement for obtaining the three-dimensional CT image of the desired image quality, and in the CT imaging measurement performed by the CT imaging portion 2, the first measurement and the second measurement are performed in succession. The measuring time of each of the first measurement and the second measurement is 4 [min]=240 [sec].

The operation of the three-dimensional X-ray CT apparatus 1 according to this embodiment is described. The operation according to this embodiment is represented by the flow chart of the processing illustrated in FIG. 3 as in the first and second embodiments. In the first measurement, the CT imaging portion 2 takes the data on N (in this case, 120) primary transmission images sequentially while rotating the gantry 11 at the rotation speed ω. When the data on the primary transmission images has been taken, the CT imaging portion 2 transfers the data on the transmission images sequentially to the image reconstruction PC 3, and in the first image reconstruction, the data acquiring section 21 of the image reconstruction PC 3 acquires the data on the transmission images. Now, the data on the k-th (where k is any integer of 1 or more and N or less) primary transmission image of the data on the N transmission images is described. As in the first and second embodiments, the data on the k-th primary transmission image is represented by $I_1(u, v, k)$. The input image data generating section 23 stores the data on the k-th primary transmission image $I_1(u, v, k)$ as the data on the k-th primary input image $J_1(u, v, k)$. In other words, $J_1(u, v, k)=I_1(u, v, k)$. As described above, the input image data generating section 23 transfers the data on the k-th primary input image $J_1(u, v, k)$ to the reconstruction processing section 24. The reconstruction processing section 24 subjects the data on the k-th primary input image $J_1(u, v, k)$ to the filtering processing and the reverse projection processing, and adds the result to the volume. The volume obtained by repeating this processing sequentially is the first three-dimensional CT image (initial three-dimensional CT image). The gantry 11 rotates continuously, and after the first measurement is finished, the CT imaging portion 2 starts the second measurement without an interval. The image reconstruction PC 3 reconstructs the first three-dimensional CT image in the first image reconstruction. The first three-dimensional CT image from the reconstruction processing section 24 is input to and stored in the storage section 22, and is input to the display portion 5 so that the first three-dimensional CT image is displayed (first display) on the display of the display portion 5 after about 4 [min] since the start of the operation, which is the initial three-dimensional CT image display.

In the second measurement, as in the first measurement, the CT imaging portion 2 takes the data on N (in this case, 120) secondary transmission images sequentially while rotating the gantry 11 at the rotation speed ω, and transfers the data on the secondary transmission images sequentially to the image reconstruction PC 3. Also in the second image reconstruction, as in the first image reconstruction, the input image data generating section 23 stores the data on the k-th secondary transmission image $I_2(u, v, k)$ as the data on the k-th secondary input image $J_2(u, v, k)$. In other words, $J_2(u, v, k)=I_2(u, v, k)$. As described above, the input image data generating section 23 transfers the data on the k-th secondary input image $J_2(u, v, k)$ to the reconstruction processing section 24. The reconstruction processing section 24 subjects the data on the k-th secondary input image $J_2(U, v, k)$ to the filtering processing and the reverse projection processing, and adds the result to the volume. The volume obtained by repeating this processing sequentially is the second three-dimensional CT image (last three-dimensional CT image). The image reconstruction PC 3 reconstructs the second three-dimensional CT image in the second image reconstruction. The second three-dimensional CT image from the reconstruction processing section 24 is input to and stored in the storage section 22, and is input to the display portion 5 so that the second three-dimensional CT image is displayed (second display) on the display of the display portion 5 after about 8 [min] since the start of the operation, which is the last three-dimensional CT image display. This completes the operation of the three-dimensional X-ray CT apparatus 1.

In the conventional three-dimensional X-ray CT apparatus, even when the main measurement is performed twice in succession, after the first measurement is performed, the computer performs the image reconstruction processing so that the three-dimensional CT image is displayed. Therefore, the downtime occurs from the end of the first measurement to the start of the second measurement. In contrast, with the three-dimensional X-ray CT apparatus 1 according to this embodiment, the CT imaging portion 2 performs the two measurements in succession so that such downtime does not occur. The image reconstruction PC 3 performs the image reconstruction processing in parallel with the measurements performed by the CT imaging portion 2, and hence the time until the three-dimensional CT image is displayed after the measurements are finished is reduced as compared to the conventional three-dimensional X-ray CT apparatus. Especially in a case where the subject undergoes a significant change with time, when the change in three-dimensional CT image is to be observed chronologically, the three-dimensional X-ray CT apparatus 1 according to this embodiment provides a significant effect.

Fourth Embodiment

Structure of a three-dimensional X-ray CT apparatus 1 according to a fourth embodiment of the present invention is the same as the structure of the three-dimensional X-ray CT apparatus 1 according to the first to third embodiments except that operation is different. The three-dimensional CT apparatus 1 according to this embodiment is different in operation from the three-dimensional X-ray CT apparatus 1 according to the third embodiment in that the input image data generating section 23 of the image reconstruction PC 3 generates the data on the secondary input images based on the data on the primary transmission images and the data on the secondary transmission images.

The operation of the three-dimensional X-ray CT apparatus 1 according to this embodiment is described. The operation according to this embodiment is represented by the flow chart of the processing illustrated in FIG. 3 as in the first to third embodiments. The primary measurement (first measurement) and the secondary measurement (second measurement) in this embodiment are the same as those of the third embodiment. Further, the first image reconstruction is also the same as that of the third embodiment. Accordingly, description is given of the generation of the data on the secondary input images in the second image reconstruction, which is different from that of the third embodiment.

In the first image reconstruction, the data on N (in this case, 120) primary input images $J_1(u, v, k)$ (=$I_1(u, v, k)$) is generated. In this case, k is any integer that satisfies the following relationship: 1≤k≤N. Therefore, the data on the N primary input images $J_1(u, v, k)$ and the data on the N secondary transmission images $I_2(u, v, k)$ are data from the same angular position of the gantry 11. In the second image reconstruction, the input image data generating section 23 weights the pieces of data from the same angular position in accordance with the rotation speed of the gantry 11 and combines the weighted pieces of data, to thereby obtain the data on the secondary input images $J_2(u, v, k)$. In other words, the data on the secondary input images $J_2(u, v, k)$ may be expressed by (Equation 1) described above. The first measurement and the second measurement have the same rotation speed ω at $T_1=t_1 \propto 1/\omega$ and $t_2 \propto 1/\omega$, which may be expressed in terms of the measuring time as: $T_1=t_1=t_2=240$. Therefore, the data on the secondary input images $J_2(u, v, k)$ may be expressed by (Equation 2) below.

$$J_2(u, v, k) = \qquad \text{[Equation 2]}$$
$$\frac{J_1(u, v, k) + I_2(u, v, k)}{2} = \frac{I_1(u, v, k) + I_2(u, v, k)}{2}$$

In the image reconstruction processing according to the third embodiment, only the data on the transmission images for the secondary measurement is used for the reconstruction of the last three-dimensional CT image. In contrast, in the image reconstruction processing according to this embodiment, not only the data on the transmission images for the secondary measurement but also the data on the transmission images for the primary measurement is used for the reconstruction of the last three-dimensional CT image. Therefore, according to the three-dimensional X-ray CT apparatus of this embodiment, in addition to the effect provided by the third embodiment, the image quality of the three-dimensional CT image displayed in displaying the last three-dimensional CT image may be improved further than in the third embodiment.

Even with the conventional three-dimensional X-ray CT apparatus, the three-dimensional CT image of the image quality that is equivalent to the second three-dimensional CT image (last three-dimensional CT image) according to this embodiment may be obtained by performing the measurement with the rotation speed that is half the rotation speed ω of the gantry in the first and second measurements according to this embodiment, the measuring range of 360°, and the measuring time of 8 [min]. However, even in this case, in the conventional three-dimensional X-ray CT apparatus, the image reconstruction processing is performed after the measurement, and hence the operating time from the start of the measurement to the display is longer than the operating time according to this embodiment. Therefore, the present invention still provides the effect of reducing the operating time. In addition, in such operation, the three-dimensional CT image is not displayed during the measurement as in the first display of this embodiment. In contrast, in this embodiment, the first display is performed about 4 [min] after the start of the measurement and before the second display is performed. Therefore, the user may judge during the operation whether the measurement situation satisfies the desired conditions, such as whether the subject is correctly held in the measuring field and whether a contrast medium and the like are correctly diffused. For example, when the measurement situation does not satisfy the desired conditions during the operation, the user may stop the operation by manual control. After stopping the operation and making sure that the measurement conditions are satisfied, the next operation may be started. Therefore, when the measurement situation does not satisfy the desired conditions, the total operating time may be reduced. Especially when the subject is a living organism or degrades significantly with time, a special effect is provided. In addition, when the subject is a living organism, a further effect of suppressing unnecessary exposure may be provided.

Fifth Embodiment

Structure of a three-dimensional X-ray CT apparatus 1 according to a fifth embodiment of the present invention is the same as the structure of the three-dimensional X-ray CT apparatus 1 according to the first to fourth embodiments except that operation is different. In the three-dimensional CT apparatus 1 according to this embodiment, the first measurement (primary measurement) and the second measurement (secondary measurement) have the same rotation speed ω of the gantry 11. The first measurement is a measurement for performing the 180° image reconstruction and has the measuring range of 180°+α. The first measurement and the second measurement constitute the measurement for performing the 360° image reconstruction and cover the measuring range of 360°. In other words, the measuring range of the second measurement is 180°−α. In this case, the first measurement and the second measurement constitute the main measurement for obtaining the three-dimensional CT image of the desired image quality, and in the CT imaging measurement performed by the CT imaging portion 2, the first measurement and the second measurement are performed in succession. The measuring time of the first measurement is 4 [min], and the total measuring time of the first measurement and the second measurement is 8 [min]=480 [sec].

The operation of the three-dimensional X-ray CT apparatus 1 according to this embodiment is described. The operation according to this embodiment is represented by the flow chart of the processing illustrated in FIG. 3 as in the first to fourth embodiments. In the first measurement, the data on M (in this case, 66) primary transmission images is taken, and in the first image reconstruction, the data on the M input images necessary for the 180° image reconstruction is generated based on the data on the M primary transmission images. The first three-dimensional CT image is obtained based on the data on the M input images, and the first display is performed. In the second measurement, the data on the remaining (N−M) (in this case, 54) secondary transmission images necessary for 360° image reconstruction is taken, and in the second image reconstruction, the data on the N input images necessary for the 360° image reconstruction is generated based on the data on N transmission images consisting of the data on the M primary transmission images and the data on the (N−M) secondary transmission images. The second three-dimensional CT image is obtained based on the data on the N input images, and the second display is performed.

The operation according to this embodiment is different from those of the third and fourth embodiments in that the 180° image reconstruction method is used, but as in the third and fourth embodiments, the first display is performed about 4 [min] after the measurement is started so that information on the three-dimensional CT image of the subject is provided to the user during the operation. Further, when the rotation speed A of the gantry 11 is the same, in the operation according to this embodiment, the initial three-dimensional CT image is displayed by the 180° image reconstruction. Therefore, a further effect of providing the image of the subject at an earlier timing after the start of the measurement than in the case where the initial display is performed by the 360° image reconstruction is provided.

Sixth Embodiment

Structure of a three-dimensional X-ray CT apparatus 1 according to a sixth embodiment of the present invention is the same as the structure of the three-dimensional X-ray CT apparatus 1 according to the first to fifth embodiments except that operation is different. The three-dimensional CT apparatus 1 according to this embodiment is different in operation from the three-dimensional X-ray CT apparatus 1 according to the third and fourth embodiments in that the CT imaging portion 2 performs I (where I is an integer of 3 or more) measurements in succession and that the image reconstruction PC 3 reconstructs the three-dimensional CT image in parallel to each of the I measurements.

Figure 4:
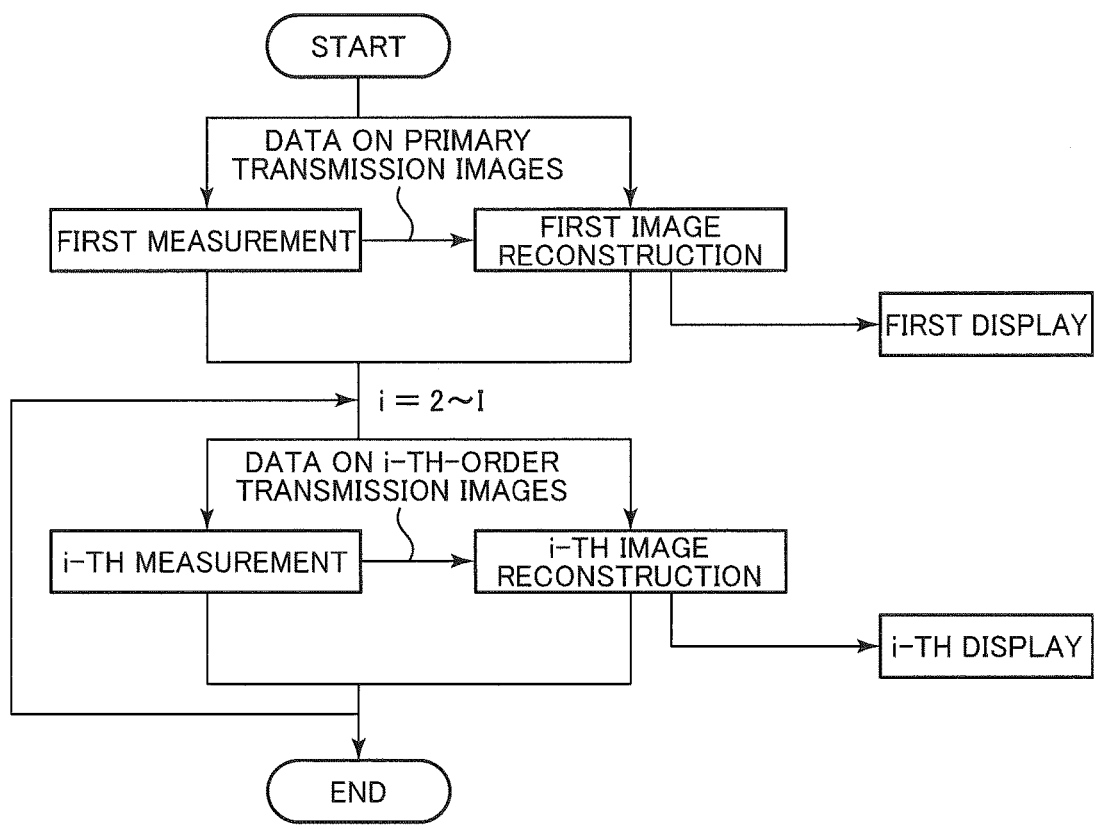
FIG. 4 is a flow chart of processing of the three-dimensional X-ray CT apparatus according to sixth to ninth embodiments of the present invention.

FIG. 4 is a flow chart of processing of the three-dimensional X-ray CT apparatus 1 according to this embodiment. In the flowchart of the processing illustrated in FIG. 4, as in the flow chart of the processing illustrated in FIG. 3, the CT imaging measurements performed by the CT imaging portion 2, which are illustrated on the left, and the three-dimensional CT image reconstruction performed by the image reconstruction PC 3, which is illustrated on the right, are performed in parallel. In this case, I measurements have the same rotation speed ω of the gantry 11 and the same measuring range of 360°. For example, it is assumed here that I=4 and that measuring time t of each measurement is t=2 [min]. Note that, the first measurement is hereinafter referred to as the primary measurement, and the second to I-th measurements are hereinafter collectively referred to as the secondary measurement. Further, each of the second to I-th measurements is a submeasurement of the secondary measurement.

In the intermediate first to (I−1)th image reconstruction, only the data on the transmission images taken in the respective corresponding measurements is used in generating the data on the input images, based on which the three-dimensional CT image is reconstructed. In other words, in the i-th (where i is 1 or more and I−1 or less) image reconstruction, the input image data generating section 23 stores data on N (in this case, 120) i-th-order transmission images (u, v, k) taken by the CT imaging portion 2 as data on i-th-order input images $J_i(u, v, k)$. In other words, $J_i(u, v, k)=I_i(u, v, k)$.

Also in the i-th image reconstruction, the input image data generating section 23 transfers the data on the k-th i-th-order input image $J_i(u, v, k)$ to the reconstruction processing section 24. The reconstruction processing section 24 subjects the data on the k-th i-th-order input image $J_i(u, v, k)$ to the filtering processing and the reverse projection processing, and adds the result to the volume. The volume obtained by repeating the processing sequentially is the i-th three-dimensional CT image, and the i-th three-dimensional CT image is displayed similarly on the display of the display portion 5 (i-th display). In this case, the I measurements are performed in succession, and hence when i is 1 or more and I−1 or less (in other words, i≠I), the i-th display is performed after the (i+1)th measurement is started. When the second display to the (I−1)th display are hereinafter referred to as intermediate display, which are performed between the initial display (first display) and the last display (I-th display), the three-dimensional CT image used in the intermediate display is reconstructed based on the data on the transmission images for each measurement (submeasurement).

In the last image reconstruction, which is the I-th image reconstruction, the I-th three-dimensional CT image (last three-dimensional CT image) is reconstructed based on all pieces of data on the transmission images taken in all the I measurements, and the I-th display, which is the last three-dimensional CT image display, is performed. In this manner, the three-dimensional CT image of high image quality may be obtained (for the reconstruction of the I-th three-dimensional CT image, see the seventh embodiment).

The three-dimensional X-ray CT apparatus 1 according to this embodiment may perform the display a larger number of times during the operation as compared to the fourth embodiment while maintaining comparable image quality of the last three-dimensional CT image and without increasing the operating time from the start of the measurement to the last display. In this embodiment, the initial display (first display) is performed about 2 [min] after the start of the measurement, and the user may judge earlier as compared to the fourth embodiment whether the measurements are performed under the desired conditions, with the result that a more special effect may be provided. Further, in the i-th display (1≤i≤I−1), the three-dimensional CT image reconstructed based only on the data on the transmission images taken in the i-th measurement is displayed, and the user may confirm the measurement situation of the subject in the respective measurements chronologically. For example, when the subject is a living organism or undergoes a significant change with time, the measurement situation of the subject may be confirmed during the measurement, and hence a special effect is provided. When the measurement situation ceases to satisfy the desired measurement conditions during the measurement, the operation may be stopped by manual control.

Seventh Embodiment

Structure of a three-dimensional X-ray CT apparatus 1 according to a seventh embodiment of the present invention is the same as the structure of the three-dimensional X-ray CT apparatus 1 according to the first to sixth embodiments except that operation is different. The three-dimensional CT apparatus 1 according to this embodiment is different in operation from the three-dimensional X-ray CT apparatus 1 according to the sixth embodiment in that the input image data generating section 23 of the image reconstruction PC 3 generates the data on the i-th-order input images (1≤i≤I) based on all of the data on the primary transmission images to the data on the i-th-order transmission images. Note that, the data on the transmission images taken in the i-th measurement is the data on the i-th-order transmission images $I_i(u, v, k)$, and the data on the input images generated by the input image data generating section 23 in the i-th image reconstruction is the data on the i-th-order input images $J_i(u, v, k)$.

The operation of the three-dimensional X-ray CT apparatus 1 according to this embodiment is described. The operation according to this embodiment is represented by the flow chart of the processing illustrated in FIG. 4 as in the sixth embodiment. In this case, the I measurements are the same as those of the sixth embodiment, and as in the sixth embodiment, the first measurement is hereinafter referred to as the primary measurement, and the second to I-th measurements are hereinafter collectively referred to as the secondary measurement. Further, each of the second to I-th measurements is a submeasurement of the secondary measurement.

The first image reconstruction is the same as that of the sixth embodiment. Therefore, description is given of the data on the input images generated by the input image data generating section 23 in the i-th (where i is an integer that satisfies image reconstruction. In the i-th image reconstruction, the input image data generating section 23 uses all of the data on the primary transmission images to the data on the i-th-order transmission images to generate the data on the i-th-order input images. The data on the primary transmission images to the data on the i-th-order transmission images from the same angular position of the gantry 11 are weighted in accordance with the rotation speed of the gantry 11 and combined, to thereby obtain the data on the i-th-order input images at the angular position. In other words, the input image data generating section 23 generates the data on the i-th-order input images as follows. The following equation is (Equation 3).

$$J_i(u, v, k) = \frac{T_{i-1} \cdot J_{i-1}(u, v, k) + t_i \cdot I_1(u, v, k)}{T_{i-1} + t_i} = \frac{\Sigma_j t_j \cdot I_j(u, v, k)}{\Sigma_j t_j}$$ [Equation 3]

As in (Equation 1), $T_{i-1}$ in (Equation 3) is a weighting factor for the data on the (i−1)th-order input image $J_{i-1}(u, v, k)$, and $t_i$ is a weighting factor for the data on the i-th-order transmission image $I_i(u, v, k)$. Further, the I measurements have the same rotation speed ω of the gantry 11 and the same measuring range so as to provide the same $t_j$ (where j is an integer of 1 or more and i or less). When $t_j$ is simply represented by t, $T_j=j \cdot t$. In this case, when the weighting factors are expressed in terms of measuring time, t=2 [min] and $T_j=2j$ [min]. Therefore, the data on the i-th-order input images $J_i(u, v, k)$ is expressed by the following equation, which is (Equation 4).

$$J_i(u, v, k) = \frac{(i-1)J_{i-1}(u, v, k) + I_1(u, v, k)}{i} = \frac{\Sigma_j I_j(u, v, k)}{i}$$ [Equation 4]

Based on the data on the i-th-order input images generated by the input image data generating section 23, the reconstruction processing section 24 reconstructs the i-th three-dimensional CT image to perform the i-th display. For example, the three-dimensional CT image used for the second display is reconstructed based on the data on the transmission images for the first measurement and the data on the transmission images for the second measurement.

As in the sixth embodiment, the three-dimensional X-ray CT apparatus 1 according to this embodiment may perform the display a larger number of times during the operation as compared to the fourth embodiment while maintaining comparable image quality of the three-dimensional CT image to be displayed at last and without increasing the operating time from the start of the measurement to the last display. Further, the i-th display (where i is 1 or more and I−1 or less) is sequentially performed during the operation, along which the image quality of the i-th three-dimensional CT image to be displayed becomes higher. The user may judge through the intermediate display whether an image of enough image quality for the purpose of the measurement is obtained. Accordingly, when the user judges that an image of enough image quality is obtained, the user may stop the operation by manual control. Therefore, a further effect of reducing the operating time is provided. Especially when the subject is a living organism or degrades significantly with time, a further special effect is provided.

Note that, in the i-th (where i is 2 or more and I or less) image reconstruction according to this embodiment, the i-th three-dimensional CT image is reconstructed based on the data on all the transmission images including the data on the primary transmission images to the data on the i-th-order transmission images. In the i-th image reconstruction, the image reconstruction is performed based on the data on all the transmission images that have already been acquired, and hence the image quality of the i-th three-dimensional CT image may be further improved. However, the present invention is not limited to this case, and the image reconstruction may be performed based on at least a part of the data on the primary transmission images to the data on the (i−1)th-order transmission images, and on the data on the i-th-order transmission images. In this case, there may be obtained the three-dimensional CT image of image quality that is higher than that of the three-dimensional CT image obtained as a result of the image reconstruction using only the data on the i-th-order transmission images. Also in this case, the pieces of data on the transmission images from the same angular position of the gantry 11 are weighted in accordance with the rotation speed of the gantry 11 and combined, to thereby generate the data on the i-th-order input images at the angular position. For example, in the i-th image reconstruction processing, the data on the i-th-order input images is generated based on the data on the (i−1)th-order transmission images and the data on the i-th-order transmission images, which are respectively acquired in the (i−1)th and i-th measurements, and hence the three-dimensional CT image of higher image quality is displayed and information on the change in the three-dimensional CT image with time is provided to the user.

Eighth Embodiment

Structure of a three-dimensional X-ray CT apparatus 1 according to an eighth embodiment of the present invention is the same as the structure of the three-dimensional X-ray CT apparatus 1 according to the first to seventh embodiments except that operation is different. The three-dimensional CT apparatus 1 according to this embodiment is different from the sixth and seventh embodiments in that the initial three-dimensional CT image is reconstructed by the 180° image reconstruction method so that the display is performed every 180°.

The operation of the three-dimensional X-ray CT apparatus 1 according to this embodiment is described. The operation according to this embodiment is represented by the flow chart of the processing illustrated in FIG. 4 as in the sixth and seventh embodiments. In this case, the I measurements have the same rotation speed ω of the gantry 11, the first measurement has the measuring range of 180°+α, the second measurement has the measuring range of 180°−α, and the third and subsequent measurements have the measuring range of 180°. For example, it is assumed here that I=4 and that the measuring time t of each measurement is t=2 [min]. Note that, to be exact, with the measuring range of the first measurement being 180°+α and the measuring range of the second measurement being 180°−α, the measuring time is about 2 [min].

Each of the first image reconstruction and the second image reconstruction is the same as the image reconstruction of the fifth embodiment. Then, in the second image reconstruction, the input image data generating section 23 generates the data on the N (in this case, 120) input images corresponding to 360° necessary for the 360° image reconstruction. As described above, once the data on the input images corresponding to 360° is generated, after the start of the third measurement, the input image data generating section 23 weights and combines the data on the taken transmission images and the data on the input images at the corresponding angular position sequentially, to thereby obtain the new data on the input images. This processing is the same as the processing performed by the input image data generating section 23 of the seventh embodiment.

Based on the data on the input images, which is generated based on the data on the transmission images up to the angular position θ=540°, the reconstruction processing section 24 reconstructs the third three-dimensional CT image to perform the third display. Further, based on the data on the input images, which is generated based on the data on the transmission images up to the angular position θ=720°, the reconstruction processing section 24 reconstructs the fourth three-dimensional CT image (last three-dimensional CT image) to perform the fourth display (last display).

The three-dimensional X-ray CT apparatus 1 according to this embodiment may perform the display a larger number of times during the operation as compared to the fifth embodiment while maintaining comparable image quality of the three-dimensional CT image to be displayed at last and without increasing the operating time from the start of the measurement to the last display. As in the seventh embodiment, the i-th display (where i is 1 or more and I−1 or less) is performed sequentially during the operation, along which the image quality of the i-th three-dimensional CT image to be displayed becomes higher. Further, when the rotation speed ω of the gantry 11 is the same, in the operation according to this embodiment, the initial three-dimensional CT image is displayed by the 180° image reconstruction. Therefore, a further effect that the images of the subject may be provided at an earlier timing from the start of the measurement and more frequently than in the sixth embodiment is provided.

Ninth Embodiment

Structure of a three-dimensional X-ray CT apparatus 1 according to a ninth embodiment of the present invention is the same as the structure of the three-dimensional X-ray CT apparatus 1 according to the first to eighth embodiments except that operation is different. In the three-dimensional CT apparatus 1 according to this embodiment, as in the first and second embodiments, the primary measurement (first measurement) serves as the measurement for preview, and the secondary measurement (second to I-th measurements) serves as the main measurement.

Description is given of operation of the three-dimensional X-ray CT apparatus 1 according to this embodiment. The operation according to this embodiment is illustrated, as with the sixth to eighth embodiments, by the flow chart of processing illustrated in FIG. 4. As in the first and second embodiments, the primary measurement (first measurement) is the measurement for preview, in which the rotation speed $ω_1$ of the gantry 11 is high and the measuring range is 180°+α. The secondary measurement may be the main measurement performed in any one of the third to eighth embodiments. In the main measurement, the rotation speed $ω_2$ of the gantry 11 is lower than that for the measurement for preview and the following relationship is satisfied: $ω_1 > ω_2$.

The image reconstruction performed by the image reconstruction PC 3 is as follows. The first image reconstruction is the same as the first image reconstruction according to the first and second embodiments. As described above, in the first image reconstruction, the data on the input images to be generated is the data on the M (in this case, 66) input images necessary for the 180° image reconstruction method. Therefore, as described in the second embodiment, the 360° image reconstruction method requires the data on the N (in this case, 120) input images. Therefore, as described in the second embodiment, in the second image reconstruction, the data on the remaining (N−M) input images is generated based on the data on the transmission images taken sequentially. Then, once the data on the input images corresponding to 360° is generated, the input image data generating section 23 sequentially weights and combines the taken data on the transmission images and the data on the input images at the corresponding angular position to obtain the new data on the input images.

According to the three-dimensional X-ray CT apparatus of this embodiment, as with the first and second embodiments, the primary measurement (first measurement) as the measurement for preview is performed so that the user may obtain a CT image of the subject earlier, and the secondary measurement (second to I-th measurements) as the main measurement is performed so that the three-dimensional CT image of the desired image quality may be obtained while the display is performed a larger number of times during the operation, to thereby provide a more significant effect.

Note that, the data on the primary transmission images acquired in the primary measurement (first measurement) as the measurement for preview is smaller in amount of information than the data on the transmission images acquired in the secondary measurement as the main measurement. In the second and subsequent image reconstruction processing, the contribution of the data on the primary transmission images in improving the image quality of the three-dimensional CT image is small. Therefore, in the second and subsequent image reconstruction processing, the data on the primary transmission images may not be used. In this case, the input image data generating section 23 uses only the data on the transmission images for the secondary measurement to generate the data on the input images for reconstructing the last three-dimensional CT image.

The three-dimensional X-ray CT apparatus 1 according to the embodiments of the present invention has been described above. When the primary measurement is the measurement for preview, it is desired that the initial display be performed soon after the start of the operation, and hence it is desired that the range of the primary measurement be the measuring range necessary for performing the 180° image reconstruction, that is, 180°+α. On the other hand, when it is preferred to perform the 360° image reconstruction, the measuring range may be 360°.

Further, the main measurement is a measurement performed for obtaining the three-dimensional CT image of the desired image quality. In order to suppress noise variation and obtain high image quality, it is desired that the measuring range be 360° multiplied by K (where K is an integer, that is, a natural number that satisfies K≥1).

In the embodiments described above, when the intermediate display is to be performed between the initial display and the last display, that is, in the i-th display ($2 \leq i \leq I-1$) illustrated in FIG. 4, the measuring range is an integer multiple of 180° when viewed from the angular position at which the measurement is started in the main measurement. In this case, the noise variation is suppressed, which is desirable in terms of the image quality of the three-dimensional CT image to be displayed, but the present invention is not limited thereto. Once the data on the input images corresponding to 360° is generated, the reconstruction processing section 24 may reconstruct the three-dimensional CT image by the 360° image reconstruction method at any time. Therefore, for example, when the intermediate display needs to be performed more frequently, the display may be performed also for the other measuring range.

Note that, in the embodiments described above, each measurement has been described for the case where the measuring range is 360° (full scan) or 180° (half scan). However, the present invention is not limited thereto as long as the data on the plurality of transmission images necessary for reconstructing the three-dimensional CT image is taken in the CT imaging measurement. For example, as in the respiration-synchronous imaging apparatus disclosed in JP 2008-228828 A1, when an animal subject performs a periodic movement such as respiration, the measuring range of one movement may be a predetermined plural number of rotations. In other words, the measuring range of one measurement may be 360°×K (where K is an integer of 2 or more). In this case, the input image data generating section 23 of the image reconstruction PC 3 selects, from among the data on the predetermined number of transmission images taken from a certain angular position, the data on a desired transmission image based on a synchronous signal of the periodic movement to generate the data on the input images. In this specification, the data on the desired transmission image is, for example, the data on the transmission image in a systole of the lung and hence the data on the transmission image in a predetermined phase of the respiratory period. In this case, a part of the data on the transmission images for the primary measurement is used to generate the data on the primary input images. In the same manner, a part of the transmission images for the secondary measurement is used to generate the data on the secondary input images in some cases, and a part of the transmission images for the primary measurement and a part of the transmission images for the secondary measurement are used to generate the data on the secondary input images in other cases.

Further, the description has been made of the case where the method of reconstructing the three-dimensional CT image is the cone-beam reconstruction method using the Feldkamp method, and of the 360° image reconstruction and the 180° image reconstruction. However, the present invention is not limited thereto and may be widely applied by using other reconstruction.

While there have been described what are at present considered to be certain embodiments of the invention, it will be understood that various modifications may be made thereto, and it is intended that the appended claims cover all such modifications as fall within the true spirit and scope of the invention.

What is claimed is:

1. A three-dimensional X-ray CT apparatus, comprising:
a CT imaging portion for continuously rotating relative angular positions of a subject and a measurement system structured for fixing the subject along center of rotation to perform a CT imaging measurement for taking data on a plurality of transmission images for reconstructing a three-dimensional CT image of the subject; and
an image reconstruction portion for reconstructing the three-dimensional CT image based on the data on the plurality of transmission images taken by the CT imaging portion,
wherein the CT imaging measurement comprises taking data on a plurality of transmission images for a primary measurement, and taking data on a plurality of transmission images for a secondary measurement, which is measured in a rotation plane common to the primary measurement in succession to the primary measurement, the data on the plurality of transmission images for the primary measurement being data necessary for the image reconstruction portion to perform 180° image reconstruction or 360° image reconstruction, and
wherein the image reconstruction portion is configured to:
reconstruct an initial three-dimensional CT image based on the data on the plurality of transmission images for the primary measurement, and display the initial three-dimensional CT image after the secondary measurement is started;
reconstruct a last three-dimensional CT image based on both the data on the plurality of transmission images for the primary measurement and the data on the plurality of transmission images for the secondary measurement, and display the last three-dimensional CT image,
wherein the image reconstruction portion comprises:
an input image data generating section for generating data on a plurality of input images based on the data on the plurality of transmission images taken by the CT imaging portion; and
a reconstruction processing section for subjecting the data on the plurality of input images to reconstruction processing to generate the three-dimensional CT image,
wherein in parallel to the primary measurement, the input image data generating section generates the data on the plurality of input images by using at least a part of the data on the plurality of transmission images for the primary measurement, and the reconstruction processing section subjects the data on the plurality of input images to the reconstruction processing to generate the initial three-dimensional CT image, and
wherein in parallel to the secondary measurement, the input image data generating section generates the data on the plurality of input images by using at least a part of the data on the plurality of transmission images for the secondary measurement, and the reconstruction processing section subjects the data on the plurality of input images to the reconstruction processing to generate the last three-dimensional CT image, and
wherein when the part of the data on the plurality of transmission images for the secondary measurement comprises data on a plurality of transmission images from the same angular position of a gantry, the input image data generating section weights the data on the plurality of transmission images in accordance with a rotation speed of the gantry and combines the weighted data on the plurality of transmission images to generate data on an input image at the angular position.

2. A three-dimensional X-ray CT apparatus, comprising:
a CT imaging portion for continuously rotating relative angular positions of a subject and a measurement system structured for fixing the subject along a center of rotation to perform a CT imaging measurement for taking data on a plurality of transmission images for reconstructing a three-dimensional CT image of the subject; and
an image reconstruction portion for reconstructing the three-dimensional CT image based on the data on the plurality of transmission images taken by the CT imaging portion,
wherein the CT imaging measurement comprises taking data on a plurality of transmission images for a primary measurement, and taking data on a plurality of transmission images for a secondary measurement, which is measured in a rotation plane common to the primary measurement in succession to the primary measurement, the data on the plurality of transmission images for the primary measurement being data necessary for the image reconstruction portion to perform 180° image reconstruction or 360° image reconstruction, and
wherein the image reconstruction portion is configured to:
reconstruct an initial three-dimensional CT image based on the data on the plurality of transmission images for the primary measurement, and display the initial three-dimensional CT image after the secondary measurement is started;
reconstruct a last three-dimensional CT image based on both the data on the plurality of transmission images for the primary measurement and the data on the plurality of transmission images for the secondary measurement, and display the last three-dimensional CT image,
wherein the image reconstruction portion comprises:
an input image data generating section for generating data on a plurality of input images based on the data on the plurality of transmission images taken by the CT imaging portion; and
a reconstruction processing section for subjecting the data on the plurality of input images to reconstruction processing to generate the three-dimensional CT image,
wherein in parallel to the primary measurement, the input image data generating section generates the data on the plurality of input images by using at least a part of the data on the plurality of transmission images for the primary measurement, and the reconstruction processing section subjects the data on the plurality of input images to the reconstruction processing to generate the initial three-dimensional CT image, and
wherein in parallel to the secondary measurement, the input image data generating section generates the data on the plurality of input images by using at least a part of the data on the plurality of transmission images for the primary measurement and at least a part of the data on the plurality of transmission images for the secondary measurement, and the reconstruction processing section subjects the data on the plurality of input images to the reconstruction processing to generate the last three-dimensional CT image, and
wherein when the part of the data on the plurality of transmission images for the primary measurement and the part of the data on the transmission images for the secondary measurement comprise data on a plurality of transmission images from the same angular position of a gantry, the input image data generating section weights the data on the plurality of transmission images in accordance with a rotation speed of the gantry and combines the weighted data on the plurality of transmission images to generate data on an input image at the angular position.

3. The three-dimensional X-ray CT apparatus according to claim 2,
wherein the primary measurement comprises a measurement for preview for judging a measurement situation,
wherein the secondary measurement comprises a main measurement for obtaining the three-dimensional CT image of desired image quality, and
wherein a rotation speed of a gantry in the primary measurement is higher than a rotation speed of the gantry in the secondary measurement.

4. The three-dimensional X-ray CT apparatus according to claim 2,
wherein the primary measurement and the secondary measurement constitute a main measurement for obtaining the three-dimensional CT image of desired image quality, and
wherein a rotation speed of a gantry in the primary measurement is equal to a rotation speed of the gantry in the secondary measurement.

5. The three-dimensional X-ray CT apparatus according to claim 2, wherein in the secondary measurement, the gantry has a rotation range of 360° multiplied by a natural number.

6. The three-dimensional X-ray CT apparatus according to claim 2, wherein when the primary measurement and the secondary measurement are combined, the gantry has a rotation range of 360° multiplied by a natural number larger than or equal to 2.

7. The three-dimensional X-ray CT apparatus according to claim 2,
wherein the secondary measurement comprises a plurality of submeasurements, and
wherein the image reconstruction portion reconstructs an intermediate three-dimensional CT image based on data on a plurality of transmission images for an initial submeasurement of the plurality of submeasurements, and displays the intermediate three-dimensional CT image after a submeasurement next to the initial submeasurement is started.

8. The three-dimensional X-ray CT apparatus according to claim 7, wherein the image reconstruction portion reconstructs the intermediate three-dimensional CT image based further on the data on the plurality of transmission images for the primary measurement.

9. The three-dimensional X-ray CT apparatus according to claim 2, wherein the subject is translationally fixed in a plane perpendicular to the center of rotation, and wherein the subject is fixed along the center of rotation.

10. A three-dimensional X-ray CT image reconstruction method with a CT imaging portion for continuously rotating relative angular positions of a subject and a measurement system structured for fixing the subject along a center of rotation to perform a CT imaging measurement for taking data on a plurality of transmission images for reconstructing a three-dimensional CT image of the subject, and with an image reconstruction portion reconstructing the three-dimensional CT image based on the taken data on the plurality of transmission images,
the CT imaging measurement comprising taking data on a plurality of transmission images for a primary measurement, and taking data on a plurality of transmission images for a secondary measurement, which is measured in a rotation plane common to the primary measurement in succession to the primary measurement, the data on the plurality of transmission images for the primary measurement being data necessary for the image reconstruction portion to perform 180° image reconstruction or 360° image reconstruction, the three-dimensional X-ray CT image reconstruction method comprising:
- a primary measurement and image reconstruction step of reconstructing an initial three-dimensional CT image based on the data on the plurality of transmission images for the primary measurement, and displaying the initial three-dimensional CT image after the secondary measurement is started; and
- a secondary measurement and image reconstruction step of reconstructing a last three-dimensional CT image based on both the data on the plurality of transmission images for the primary measurement and the data on the plurality of transmission images for the secondary measurement, and displaying the last three-dimensional CT image, wherein the image reconstruction steps comprise
- an input image data generating step for generating data on a plurality of input images based on the data on the plurality of transmission images taken by the CT imaging portion; and
- a reconstruction processing step for subjecting the data on the plurality of input images to reconstruction processing to generate the three-dimensional CT image, wherein in parallel to the primary measurement, the input image data generating step generates the data on the plurality of input images by using at least a part of the data on the plurality of transmission images for the primary measurement, and the reconstruction processing step subjects the data on the plurality of input images to the reconstruction processing to generate the initial three-dimensional CT image, and wherein in parallel to the secondary measurement, the input image data generating step generates the data on the plurality of input images by using at least a part of the data on the plurality of transmission images for the primary measurement and at least a part of the data on the plurality of transmission images for the secondary measurement, and the reconstruction processing step subjects the data on the plurality of input images to the reconstruction processing to generate the last three-dimensional CT image, and wherein when the part of the data on the plurality of transmission images for the primary measurement and the part of the data on the transmission images for the secondary measurement comprise data on a plurality of transmission images from the same angular position of a gantry, the input image data generating step weights the data on the plurality of transmission images in accordance with a rotation speed of the gantry and combines the weighted data on the plurality of transmission images to generate data on an input image at the angular position.

11. A non-transitory computer-readable medium including computer-executable instructions for execution on a computer which is included in a three-dimensional X-ray CT apparatus with a CT imaging portion for continuously rotating relative angular positions of a subject and a measurement system structured for fixing the subject along a center of rotation to perform a CT imaging measurement for taking data on a plurality of transmission images for reconstructing a three-dimensional CT image of the subject, and with an image reconstruction portion reconstructing the three-dimensional CT image based on the taken data on the plurality of transmission images, the CT imaging measurement comprising taking data on a plurality of transmission images for a primary measurement, and taking data on a plurality of transmission images for a secondary measurement, which is measured in a rotation plane common to the primary measurement in succession to the primary measurement, the data on the plurality of transmission images for the primary measurement being data necessary for the image reconstruction portion to perform 180° image reconstruction or 360° image reconstruction, wherein the computer-readable instructions, when executed by the computer, cause the computer to perform:

image reconstructing an initial three-dimensional CT image based on the data on the plurality of transmission images for the primary measurement, and displaying the initial three-dimensional CT image after the secondary measurement is started; and image reconstructing a last three-dimensional CT image based on both the data on the plurality of transmission images for the primary measurement and the data on the plurality of transmission images for the secondary measurement, and displaying the last three-dimensional CT image, wherein the image reconstructing steps comprise
- an input image data generating step for generating data on a plurality of input images based on the data on the plurality of transmission images taken by the CT imaging portion; and
- a reconstruction processing step for subjecting the data on the plurality of input images to reconstruction processing to generate the three-dimensional CT image, wherein in parallel to the primary measurement, the input image data generating step generates the data on the plurality of input images by using at least a part of the data on the plurality of transmission images for the primary measurement, and the reconstruction processing step subjects the data on the plurality of input images to the reconstruction processing to generate the initial three-dimensional CT image, and wherein in parallel to the secondary measurement, the input image data generating step generates the data on the plurality of input images by using at least a part of the data on the plurality of transmission images for the primary measurement and at least a part of the data on the plurality of transmission images for the secondary measurement, and the reconstruction processing step subjects the data on the plurality of input images to the reconstruction processing to generate the last three-dimensional CT image, and wherein when the part of the data on the plurality of transmission images for the primary measurement and the part of the data on the transmission images for the secondary measurement comprise data on a plurality of transmission images from the same angular position of a gantry, the input image data generating step weights the data on the plurality of transmission images in accordance with a rotation speed of the gantry and combines the weighted data on the plurality of transmission images to generate data on an input image at the angular position.

* * * * *